US009035778B2

(12) United States Patent
Howie et al.

(10) Patent No.: US 9,035,778 B2
(45) Date of Patent: May 19, 2015

(54) MONITORING VITAL SIGNS BASED ON SENSED CHANGES TO AN ELECTRICAL FIELD

(71) Applicant: Life Detection Systems, LLC, Danville, CA (US)

(72) Inventors: Eric Howie, San Jose, CA (US); Guy McIlroy, Los Gatos, CA (US); John Haggis, San Jose, CA (US); Nanci Yuan, Menlo Park, CA (US)

(73) Assignee: LIFE DETECTION SYSTEMS, INC., Danville, CA (US)

( * ) Notice: Subject to any disclaimer, the term of this patent is extended or adjusted under 35 U.S.C. 154(b) by 0 days.

(21) Appl. No.: 13/841,959

(22) Filed: Mar. 15, 2013

(65) Prior Publication Data

US 2014/0055269 A1   Feb. 27, 2014

Related U.S. Application Data

(60) Provisional application No. 61/693,194, filed on Aug. 24, 2012.

(51) Int. Cl.
*G08B 23/00* (2006.01)
*G01R 29/08* (2006.01)
(Continued)

(52) U.S. Cl.
CPC ............ *G01R 29/08* (2013.01); *G08B 21/0211* (2013.01); *G08B 21/02* (2013.01); *A61B 5/7203* (2013.01); *A61B 5/746* (2013.01)

(58) Field of Classification Search
CPC .................. G08B 21/0211; A61B 2562/0219; A61B 2562/028
USPC ................ 340/573.1; 600/345, 483, 527, 587
See application file for complete search history.

(56) References Cited

U.S. PATENT DOCUMENTS 6,679,830 B2   1/2004   Kolarovic et al.
7,173,525 B2   2/2007   Albert
(Continued)

FOREIGN PATENT DOCUMENTS

FR           2923150 A1    5/2009
WO    WO-03/048789 A2     6/2003

OTHER PUBLICATIONS

"Heartfelt tm Infant Vitals & Video Monitoring System", [online]. (c) 2012 PREE Corporation. [retrieved on Sep. 20, 2012]. Retrieved from the Internet: <URL: http://www.technophysics.com/technology/heartfelt_baby_monitor>, (2012), 4 pgs.

(Continued)

*Primary Examiner* — John A Tweel, Jr.
(74) *Attorney, Agent, or Firm* — Wilmer Cutler Pickering Hale and Dorr LLP

(57) ABSTRACT

Methods and systems for monitoring a well-being of a target are disclosed. In a method embodiment, data representing a process electric potential signal is received by a computer system. The process electric potential signal may be generated at least in part by one or more electric potential sensors in response to the detection of a change in an electric field of a target spaced apart from the one or more electric potential sensors. The method may further include identifying, using the computer system and based at least in part on the data electronically received by the computer system, a recurring pattern in the received data. The method may also include determining, using the computer system and based at least in part on the received data, whether a deviation from the recurring pattern transgresses a threshold. The deviation may comprise a subset of the data electronically received by the computer system.

36 Claims, 14 Drawing Sheets

(51) Int. Cl.
*G08B 21/02* (2006.01)
*A61B 5/00* (2006.01)

(56) References Cited

U.S. PATENT DOCUMENTS

| | | | |
|---|---|---|---|
| 7,383,071 B1 * | 6/2008 | Russell et al. | 600/345 |
| 7,445,605 B2 * | 11/2008 | Overall et al. | 600/527 |
| 7,885,700 B2 | 2/2011 | Clark et al. | |
| 8,057,388 B1 * | 11/2011 | Russell et al. | 600/345 |
| 2002/0013538 A1 | 1/2002 | Teller | |
| 2004/0100376 A1 | 5/2004 | Lye et al. | |
| 2004/0260346 A1 * | 12/2004 | Overall et al. | 600/508 |
| 2006/0154642 A1 | 7/2006 | Scannell | |
| 2008/0007445 A1 | 1/2008 | Leach, Jr. et al. | |
| 2009/0048500 A1 | 2/2009 | Corn | |
| 2009/0240160 A1 | 9/2009 | Thompson et al. | |
| 2009/0318779 A1 | 12/2009 | Tran | |
| 2013/0267791 A1 * | 10/2013 | Halperin et al. | 600/300 |

OTHER PUBLICATIONS

"International Application Serial No. PCT/US2013/055068, International Search Report mailed Jan. 7, 2014", 5 pgs.
"International Application Serial No. PCT/US2013/055068, Invitation to Pay Additional Fees and Partial Search Report mailed Oct. 31, 2013", 4 pgs.
"International Application Serial No. PCT/US2013/055068, Written Opinion mailed Jan. 7, 2014", 7 pgs.
"Non-Contact Monitor for Infants at Risk", SBIR/STTR.Award. [online]. [retrieved on Sep. 20, 2012]. Retrieved from the Internet: <URL: http://www.sbir.gov/sbirsearch/detail/156740>, 2 pgs.
"PREE Corporation's Heartfelt Infant Vitals and Video Monitoring System is Now in Pre-Sales", PREE Corporaton Press Release, [online] [retrieved Sep. 20, 2012]. Retrieved from the Internet: <URL: http://www.businesswire.com/news/home/20120215006285/en/PREE-Corporations-Heartfelt-Infant-Vitals-Video-Monitoring>, (Feb. 15, 2012), 1 pg.
"Standards for assessing, measuring and monitoring vital signs in infants, children and young people", (c) 2011 Royal College of Nursing, [online]. [retrieved Sep. 20, 2012]. Retrieved from the Internet: <URL: http://www.rcn.org.uk/__data/assets/pdf_file/0004/114484/003196.pdf>, (2011), 16 pgs.
Beardsmore-Rust, S. T., "Remote applications of electric potential sensors in electrically unshielded environments", PhD. Thesis, University of Sussex. [online]. [retrieved on Sep. 20, 2012]. Retrieved from the Internet: <URL: http://sro.sussex.ac.uk/2407/1/Beardsmore-Rust%2C_Sam.pdf>, (Apr. 2010), 185 pgs.
Buckley, P., "Plessey EPIC sensor makes a heart monitor in a wristwatch", [online]. EE Times Europe. [retrieved on Sep. 20, 2012]. Retrieved from the Internet: <URL: http://www.eetimes.com/electronics-news/4372353/Plessey-reveals-EPIC-sensor-technology-to-create-a-heart-monitor-in-a-wristwatch>, (May 6, 2012), 2 pgs.
Connor, S., "EPIC—Introducing Plessey's multi award winning EPIC Sensor and its many applications", [online]. [retrieved Sep. 20, 2012]. Retrieved from the Internet: <URL: http://www.plesseysemiconductors.com/products/epic/technical/>, (2012), 5 pgs.
Connor, S., et al., "EPIC: A New Epoch in Electric Potential Sensing", [online]. [retrieved on Sep. 20, 2012]. Retrieved from the Internet: <URL: http://www.sensorsmag.com/sensors/electric-magnetic/epic-a-new-epoch-electric-potential-sensing-8961>, (Sep. 1, 2011), 4 pgs.
German-Sallo, Z., "Applications of Wavelet Analysis in ECG Signal Processing", PhD. Thesis, Technical University of Cluj-Napoca, (2005), 11 pgs.
German-Sallo, Z., "Processing of ECG Signals Using Wavelet Analysis", *Acta Electrotehnica*, vol. 46(3), (2005), 135-140.
Saritha, C., et al., "ECG Signal Analysis Using Wavelet Transforms", *Bulg. J. Phys., 35*, (2008), 68-77.
Venkataramanan, M., "Biosensor can monitor your heartbeat from a distance", [online]. (c) Copyright Reed Business Information Ltd. [retrieved on Sep. 20, 2012], Retrieved from the Internet: <URL: http://www.newscientist.com/blogs/onepercent/2011/11/sensor-monitors-your-heartbeat.html>, (Nov. 16, 2011), 6 pgs.
Yan, Y., et al., "Verification of a non-contact vital sign monitoring system using an infant simulator", *Con. Proc. IEEE Eng. Med. Biol. Soc. 2009*, (Abstract Only), [online]. [retrieved on Sep. 20, 2012]. Retrieved from the Internet: <URL:http://www.ncbi.nlm.nih.gov/pubmed>, (2009), 1 pg.
Yan, Y., et al., "Verification of a Non-Contact Vital Sign Monitoring System Using an Infant Simulator", *Con. Proc. IEEE Eng. Med. Biol. Soc., 31st Annual International Conference of the IEEE EMBS*, (Minneapolis, MN, Sep. 2-6, 2009, (2009), 4836-4839.

* cited by examiner

Saturation 60Hz ▮▶ , bandpass output ▷

Suppressed signal 1, suppressed bandpass 2

Final output at 50mV/div and time scale of 20ms/div

Final output at 50mV/div and time scale of 200ms/div

MONITORING VITAL SIGNS BASED ON SENSED CHANGES TO AN ELECTRICAL FIELD

CROSS-REFERENCE TO RELATED APPLICATIONS

This application claims the benefit of U.S. Provisional Application No. 61/693,194, filed Aug. 24, 2012, entitled "ANALYZING ELECTRICAL FIELDS ASSOCIATED WITH LIFE FORMS," which is incorporated herein by reference in its entirety.

TECHNICAL FIELD

This application relates generally to the technical field of monitoring systems, in one specific example, to a baby monitoring system having an alarm that is triggered based on sensed changes to an electrical field.

BACKGROUND

The performance of a variety of monitoring systems may be affected by where a sensor or its parts are placed relative to a target that is being monitored. For example, certain monitoring systems may require a sensor to be in physical contact with a target and may further require a part (e.g., a power or data cable) to be connected from a sensor to a monitoring device. Installing sensor parts in a baby crib may be contrary to expert advice to keep the baby crib free of such objects (e.g., based on the sensor parts constituting a strangulation or suffocation hazard). Alternatively, the sensor may require wireless communication between a sensor and a monitoring device, thereby introducing potentially harmful or interfering communication waves (e.g., radio frequency waves, microwave communication waves, etc.) in close vicinity to the baby, another target of the monitoring system, or other electronic equipment.

BRIEF DESCRIPTION OF THE DRAWINGS

Some embodiments are illustrated by way of example and not limitation in the figures of the accompanying drawings in which.

DETAILED DESCRIPTION

In the following description, for purposes of explanation, numerous specific details are set forth in order to provide an understanding of various embodiments of the present subject matter. It will be evident, however, to those skilled in the art that various embodiments may be practiced without these specific details.

In various embodiments, a method is disclosed that may be used, for example, to monitor a target. The method may include electronically receiving, by a computer system, data representing a process electric potential signal. The process electric potential signal may be generated at least in part by one or more electric potential sensors in response to the detection of a change in an electric field of a target spaced apart from the one or more electric potential sensors. The method may further include identifying, using the computer system and based at least in part on the data electronically received by the computer system, a recurring pattern in the data electronically received by the computer system, a recurring pattern in the data representing a process electric potential signal. The method may also include determining, using the computer system and based at least in part on the data electronically received by the computer system, whether a deviation from the recurring pattern transgresses a threshold. The deviation may comprise a subset of the data electronically received by the computer system.

In certain method embodiments, a pattern of disturbances in an electrical field is monitored. An anomaly in the pattern of the disturbances in the electrical field is detected. A correspondence between the anomaly and the threat to the well-being of the target is determined. An alarm is generated based on the determining of the correspondence.

Figure 1:
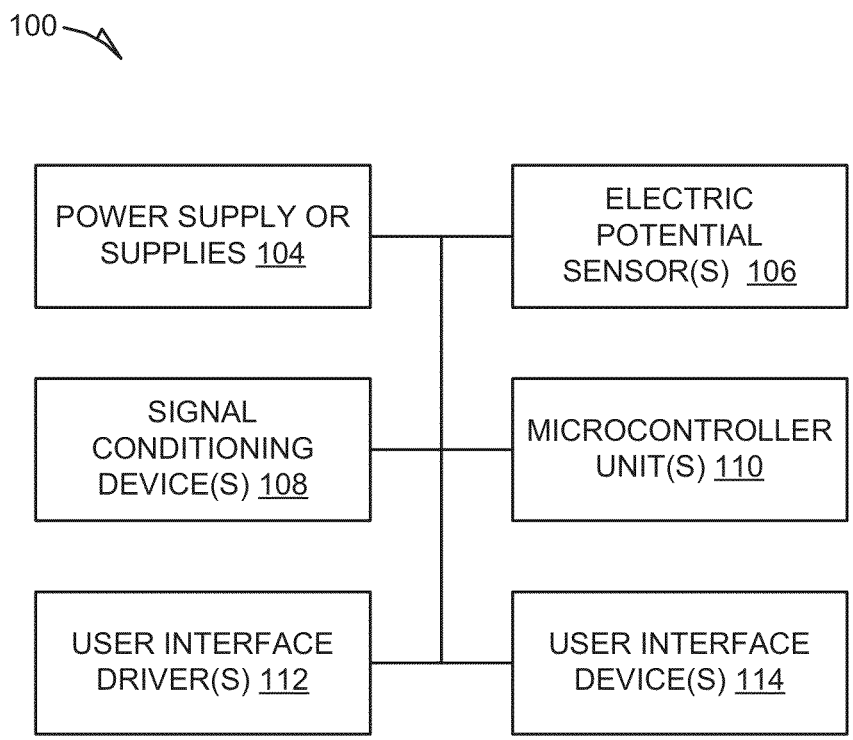
FIG. 1 is a block diagram depicting an example embodiment of a portion of a system capable of monitoring disturbances in electric fields.

Methods and various embodiments disclosed herein may be implemented as a computer system having one or more modules (e.g., hardware modules or software modules). Furthermore, methods and various embodiments disclosed herein may be embodied as instructions stored on a computer-readable medium that, when executed by one or more processors, cause the one or more processors to perform the instructions. FIG. 1 is a block diagram depicting an example embodiment of a portion of a system 100 generally capable of monitoring disturbances in electrical fields. In this example, monitoring system 100 includes multiple modules 104, 106, 108, 110, 112, and 114. Although the illustrated embodiment includes example modules 104, 106, 108, 110, 112, and 114, any suitable module(s) may be used including, for example, additional or alternative modules. As used herein, the term module generally refers to any suitable combination of hardware, software, or firmware configured to facilitate the monitoring of electrical fields.

Module 104 may be, or may include, one or more power supplies that may be configured, for example, to receive power from an energy source (e.g., a battery, an alternating current (AC) line, and so on) and to supply power to various other modules of the monitoring system 100 (e.g., at specific voltages required by the other components). For example, module 104 may include a power supply having a three Volt (3V) or similar input. Furthermore, module 104 may include a buck-boost converter configured to minimized losses from input voltage to source load.

Module 106 may include may include one or more electric field disturbance sensors. Certain electric field disturbance sensors may be configured, for example, to detect fluctuation in an electric field and, in response, to generate a detection signal corresponding to the detected fluctuation. As explained further below, system 100 may be capable of associating certain detected electric field fluctuations with a particular target or with a particular movement of that target. As used herein, a target is any person or thing that is capable of disturbing an electric field. In a particular embodiment, for example, a target may be a patient undergoing a particular medical observation facilitated by system 100.

In various embodiments, the electric field disturbance sensor(s) of module 106 behave as a high impedance antenna capable of sensing electric potential disturbance within the vicinity, including those generated remotely from the electric field disturbance sensor(s). For example, certain electric field disturbance sensor(s) of module 106 may detect electric potential at a distance of up to several inches, several feet, or more. In certain applications, the ability to remotely detect electric potential disturbance within the vicinity may facilitate three-dimensional positional analysis of a target. As an example, whenever a human body moves, it may generate electric potential variations with specific characteristics that depend on the nature of the movement. Thus, heart movements, eye movements, lung movements, and limb movements, for example, may generate electric potential signals that are detectable by certain electric field disturbance sensors(s), even if positioned remotely from the target.

Any suitable electric field disturbance sensor may be used by module 106. For example, module 106 may include one or more electric field disturbance sensor(s) based on or substantially similar to the Electric Potential Integrated Circuit (EPIC) technology of Plessey Semiconductors Ltd. or to certain electric field sensors of Campbell Scientific (e.g., CS110).

In a particular embodiment, module 106 is communicatively coupled to module 108, such that a detection signal generated at module 106 may be communicated (e.g., wirelessly or by wired communication) to module 108.

Module 108 may be, or may include, one or more signal conditioning devices configured to condition or manipulate a detection signal received from module 106 into a conditioned signal that may be used, for example, to facilitate certain signal processing by system 100. Any suitable signal conditioning may be used including, for example, a combination of various signal conditioning. For example, the signal conditioning device(s) 108 may include an operational amplifier (op-amp) configured to amplify an analog detection signal received from the electric field disturbance sensors(s) 106. As another example, the signal conditioning device(s) 108 may include one or more filters configured to reduce noise in a detection signal received from the electric field disturbance sensors(s) of module 106, as described in more detail below. As yet another example, module 108 may be capable of receiving an analog detection signal from module 106 and performing an analog-to-digital conversion. Thus, in a particular embodiment, module 108 generally receives as an input a detection signal from module 106 and, in response, generates an output as a conditioned signal.

In a particular embodiment, module 108 is communicatively coupled to module 110, such that a conditioned signal conditioned by module 108 may be communicated (e.g., wirelessly or by wired communication) to module 110.

Module 110 may be, or may include, one or more microcontroller unit(s) configured to process signals received from one or more other modules of monitoring system 100. For example, one or more microcontroller unit(s) of module 110 may receive as an input a conditioned signal from the signal conditioning device(s) of module 108. The microcontroller unit(s) may then process the received conditioned signal, as described in more detail below.

In a particular embodiment, the processing effected by module 110 may include identifying whether a conditioned signal received as a data input from module 108 corresponds to a vital sign of a target and, if so, determining whether the data indicates that the well-being of the target is threatened. As used herein, a vital sign may not only include physiological vital signs (e.g., heart movements, blood movements, lung movements, muscle movements, eye movements, brain activity, limb movements, body movements, and so on), but also non-physiological vital signs (e.g., measurements pertaining to the health of a vehicle or building). For example, the health of a building may be monitored based on sensing of termites within the walls of the building. Or the health of a vehicle (or other inanimate object) may be determined based on the sensing a change in an electric field disturbance caused by electric components of the vehicle (or object).

In a particular embodiment, module 110 is communicatively coupled to module 114, such that a communication generated at module 110 may be communicated (e.g., wirelessly or by wired communication) to module 114. For example, the microcontroller unit(s) of module 110 may be configured to communicate a result of its signal processing to one or more user interface device(s) 114 (e.g., via one or more respective user interface driver(s) 112). For example, if the microcontroller unit(s) of module 110 determine that the well-being of the target is threatened, the microcontroller unit(s) may send a communication that activates a siren or other alarm, or activates or changes a color of a light-emitting diode (LED) of the monitoring system 100.

In a particular embodiment, the user interface driver(s) may receive communications from the microcontroller unit(s) of module 110 and translate them into a format that is appropriate for the particular user interface device(s) of module 114 on which the status of the monitoring system 100 may be represented. The user interface device(s) of module 114 may include one or more sensitivity controls (e.g., dials) configured to enable a user to control the sensitivity of the electric field disturbance sensor(s) of module 106 either singularly or collectively (e.g., at particular frequencies).

In certain embodiments, the user interface device(s) of module 114 includes one or more indicators (e.g., via a display or LED) configured to indicate which ones of potentially multiple types of signals that the system 100 is currently able to detect or not able to detect with respect to a target (e.g., whether the system 100 is able to identify signals pertaining to the heart, lungs, brain, limbs, body, etc.). Thus, a user of the system 100 may be able to configure the electric field disturbance sensor(s) based on information that the user receives via the user interface device(s) 114.

Figure 2:
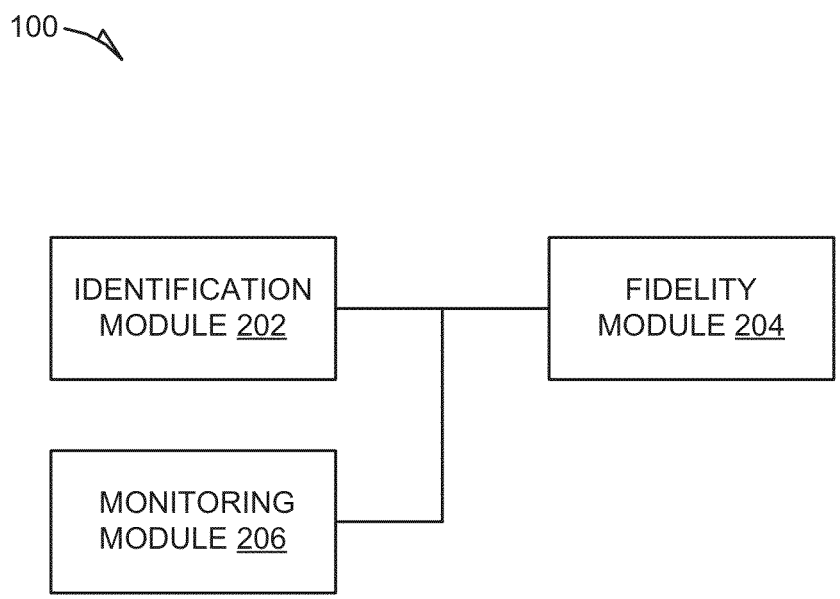
FIG. 2 is a block diagram depicting certain other example modules that may be used by the system of FIG. 1 according to a particular embodiment.

FIG. 2 is a block diagram depicting certain example modules of the system 100 of FIG. 1 according to a particular embodiment. At least a portion of certain modules may be embodied as instructions that are implemented by the microcontroller unit(s) of module 110. The system 100 may include an identification module 202 that is configured to identify vital sign electric potential signals from a process electric signal. The system 100 may include a fidelity module 204 that is configured to increase a fidelity of a candidate potential electric signal derived from a process electric potential signal (e.g., such that the candidate potential electric signal may be disambiguated from an additional candidate potential electric signal such that it may be identified as a vital sign electric potential signal), as described in more detail below.

Figure 3:
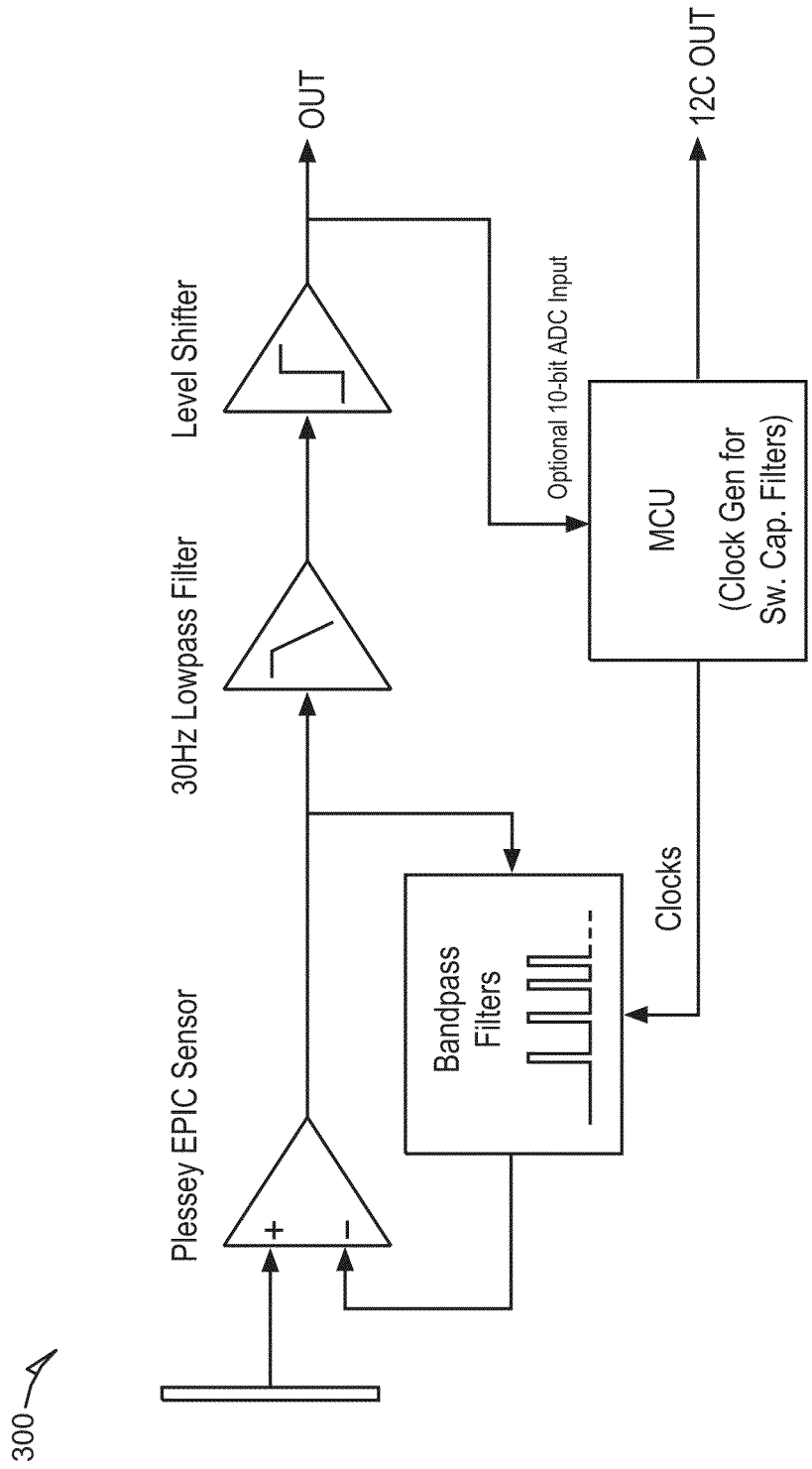
FIG. 3 is a block diagram depicting an example embodiment of a physio/motion sensor board that may be used by the system of FIG. 1 to monitor disturbances in electrical fields.

FIG. 3 is a block diagram depicting an example embodiment of a physio/motion sensor board 300 that is configured to monitor disturbances in electrical fields. The physio/motion sensor board 300 may comprise a high-impedance sensor module (e.g., a Plessey EPIC "EPS" (Electric Potential Sensor)) and certain filtering capability. The filtering capability may be configured, for example, to enhance the sensing capacity to low-level signals in the presence of high-level background electrical noise. The physio/motion sensor board 300 may also include a 30 Hz analog low-pass filter at the output and a level shifter/gain block to bring it to a 0-3.3V scale, which in certain instances may facilitate digitization by a microcontroller or DSP.

The noise suppression may work by using switched-capacitor filter chips in an inverse-notch filter (tight bandpass) configuration of 60 Hz and several of its harmonics, fed back into the negative feedback input of the high-impedance sensor. In effect, this creates a multiple-notch filter for the 60 Hz spectrum that could saturate the sensitive, high-gain amplifier at the front end.

The analog low-pass filter may be configured, for example, to filter out digital clock bleed into the signal and/or other high frequency interference, while passing physiological signals (EKG, respiration) and very low-frequency movement.

Figure 4:
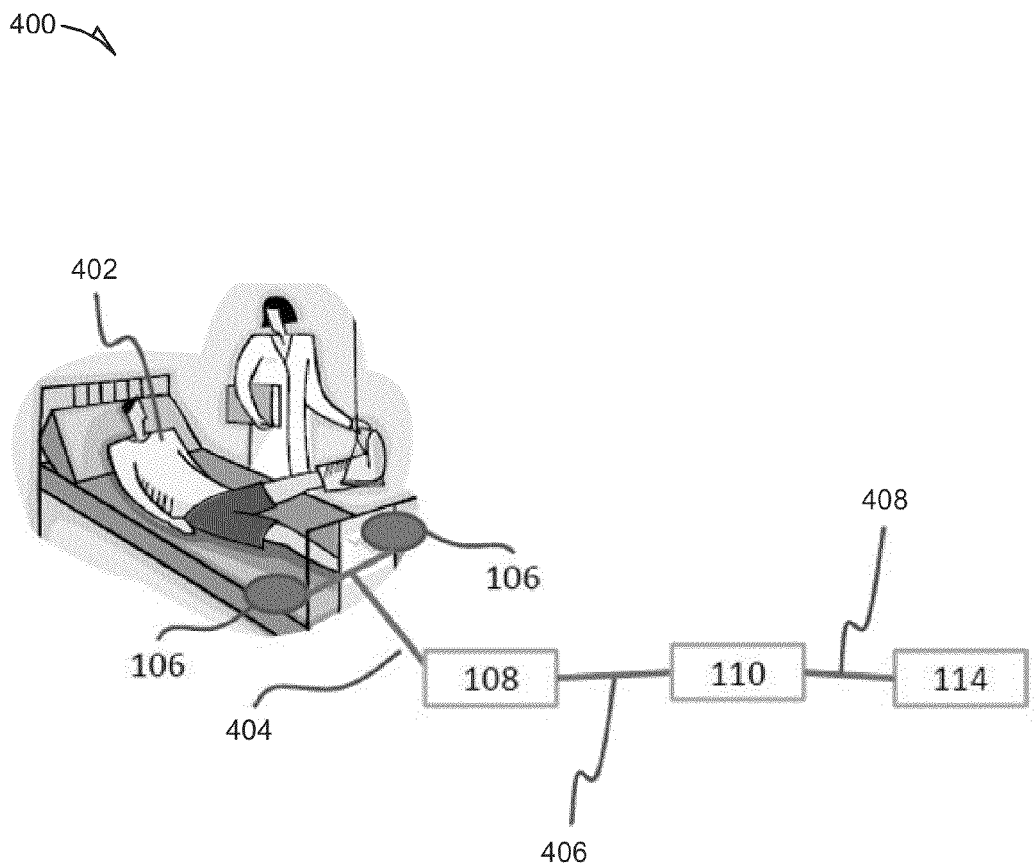
FIG. 4 is a diagram of example interactions of certain modules of FIG. 1, which interactions may occur during the monitoring of electric field disturbances associated with a target.

FIG. 4 is an interaction diagram of example interactions of certain modules of FIG. 1. Certain interactions may occur, for example, during the monitoring of electric field disturbances associated with a target. As shown in FIG. 4, the electric field disturbance sensor(s) 106 are in communication with the signal conditioning device(s) 108 via communication pathway 404, the signal conditioning device(s) 108 are in communication with the microcontroller unit(s) 110 via communication pathway 406, and the microcontroller unit(s) 110 are in communication with the user interface device(s) 114 via communication path 408.

Figure 5:
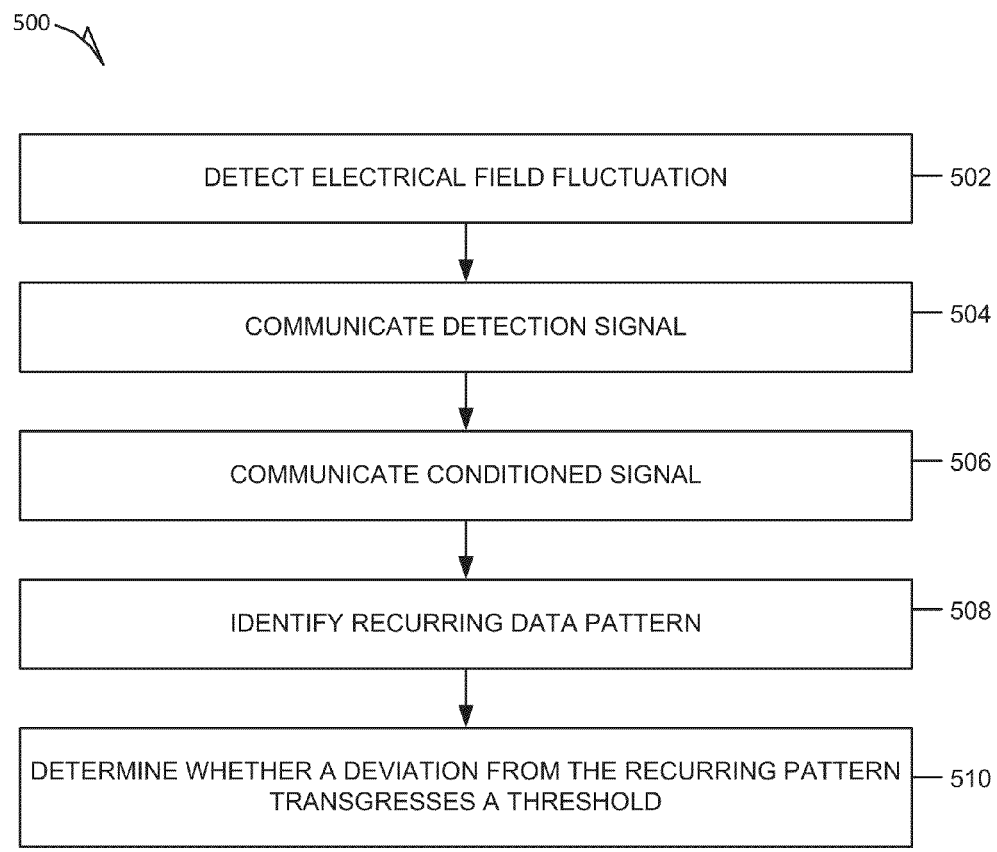
FIG. 5 is a flowchart of an example embodiment of a method of identifying electrical potential signals or electric field disturbance signals as pertaining to certain vital signs of a target.

FIG. 5 is a flowchart of an example embodiment of a method 500 for identifying electrical potential signals, sometimes referred to as electric field disturbance signals, as pertaining to certain vital signs of a target. In various embodiments, the method 500 may be implemented by one or more of the modules of FIG. 1-5. At operation 502, a fluctuation in an electric field is detected. As shown in FIG. 4, for example, a particular movement of a target 402 (e.g., one or more of a particular heart movement, eye movement, lung movement, limb movement) may generate electric potential signals that are detectable by one or more electric field disturbance sensor(s) 106, even if the sensor(s) are positioned remotely from the target.

In response to the detected fluctuation, a detection signal corresponding to the detected fluctuation may be communicated in operation 504. For example, module 106 may communicate the detection signal to module 108, as explained previously with reference to FIG. 1 and shown by way of example in FIG. 4 by a detection signal 404.

At operation 506, a conditioned signal may be communicated based at least in part on the detection signal communicated in step 504. As explained previously with reference to FIG. 1 and as shown in FIG. 4, for example, module 108 may receive a detection signal 404 as an input, condition the received signal, and communicate a corresponding conditioned signal 406 as an output. In particular embodiments, the signal conditioning effected at operation 506 may include filtration, amplification, conversion (e.g., inversion or analog-to-digital conversion), any combination thereof, or any other suitable signal conditioning that effects a transformation of the signal, as explained previously with reference to FIG. 1.

In certain instances, a detection signal 404 conditioned at operation 506 may include data in the 50 Hz or 60 Hz frequencies. Thus, the signal being conditioned may include disturbances in an electric field that are potentially caused at least in part by mains (or general-purpose) electricity or electric alternating-current (AC), possibly in addition to disturbances caused by the target 402. However, instead of eliminating all signals in the 50 Hz or 60 Hz frequencies from consideration as possibly pertaining to the well-being of the target 402, certain filter algorithms may be used to disambiguate signals corresponding to electric field disturbances created by the target 402 from electric field disturbances created by a standard electric power source (e.g., module 104).

In various embodiments, active filtering is performed at operation 506. Active filtering may include filtering ambient electric field disturbances from electric field disturbances caused by the target 402. Such filtering may be effected, for example, by comparing a detection signal from a first electric field disturbance sensor that is configured or positioned to capture ambient electric field disturbances in an environment of the target (but not the target itself) and a detection signal from a second electric field disturbance sensor that is configured or positioned to capture electric field disturbances of the target within the environment. In various embodiments, a single electric field disturbance sensor is used to capture both the ambient electric field disturbances and the electric field disturbances created by the target (e.g., over separate time periods). For example, a monitoring system 100 having a single electric field disturbance sensor may be placed into the environment before the target is placed in the environment for a time period (e.g., an hour). After capturing and storing data corresponding to ambient electric field disturbances in the environment, the target may be placed into the environment. Then the monitoring system 100 may use the same electric field disturbance sensor to identify electric field disturbances in the environment, which include those generated by the target. The monitoring system may then use the data pertaining to the previously identified ambient electric field disturbances to identify those electric field disturbances that are most likely created by the target. Additional processing may be used to identify particular signals as corresponding to vital signs of the target, as explained further below.

In a particular embodiment, the conditioned signal 406 is communicated at operation 506 in the form of data representing a fluctuation in an electric field that had been detected, for example, at operation 502. In certain embodiments, the data communicated at operation 506 may be computer-readable and may have a particular format suitable for processing at subsequent operations. For example, the communicated data may have a format suitable for processing by one or more microcontroller unit(s) of module 110.

At operation 508, a recurring pattern of a signal may be identified. For example, as explained previously with reference to FIG. 1, one or more microcontroller unit(s) of module 110 may perform one or more operations that facilitate identifying a recurring pattern of a signal. In certain instances, the signal analyzed for a recurring pattern may be a conditioned signal 406 in the form of computer-readable data having a particular format suitable for processing by one or more microcontroller unit(s) of module 110.

In certain embodiments, a recurring pattern may be identified at operation 508 at least in part using one or more filter algorithms. For example, a notch (50/60 Hz), low pass, high pass, any combination thereof, or other filter algorithm(s) may be used. Certain filters may be digitally implemented (e.g., by module 110 according to best practice guidelines).

In certain instances, multiple patterns may be identified at operation 508. For example, a separation analysis may be used to identify various patterns that, in certain instances, may have substantially concurrent time domain components. The various patterns may correspond to one or more respective vital signs of a target (e.g., heartbeat and breathing occurring substantially simultaneously). In a particular embodiment, the monitoring system 100 (e.g., via wavelet analysis) separates electric field disturbances pertaining to general movements of the body of a human target (as a whole) from electric field disturbances pertaining to movements of parts (e.g., heart or eye movements) of the body of the target. In various embodiments, this separation analysis may be applied to data having 50 Hz and 60 Hz components in the frequency domain; however, any suitable frequency or range of frequencies may be used. Additional detail regarding identifying multiple patterns, according to particular embodiments, is explained further below with reference to FIG. 6.

In a particular embodiment, identification of a pattern at operation 508 in multiple domains (e.g., frequency and time domains) may be achieved at least in part using wavelet transforms including, for example, Fourier Wavelet Transforms. Certain wavelet transforms may be used to decompose data into a series of functions, which may include sine and cosine functions. In particular embodiments, use of wavelet functions to identify a particular pattern may facilitate matching the characteristics of intermittent signals to the characteristics of the vital signs sought to be detected.

In certain instances, the identification of a pattern at operation 508 may include associating a particular data pattern with a respective vital sign of a target. For example, analysis of historical data may be incorporated into an algorithm for identifying a subset of data corresponding to a vital sign of a target. In certain instances, the historical data may include a property corresponding to a previously identified vital sign, such that the historical data may be used as a basis of comparison in identifying patterns associated with that vital sign. Various identified patterns may be reduced to fundamental target signals and stored for purposes of later comparison with other datasets derived from the detected electrical field disturbances caused by a target. Additional detail regarding associating a particular data pattern with a respective vital sign of a target is explained further below with reference to FIG. 6.

In particular embodiments, the recurring pattern identified at operation 508 may involve a predictable pattern that may have an expected duration but may have time domain components indicating occurrences at relatively random intervals. For example, a pattern may be identified at operation 508 as corresponding to a limb movement or eye movement that happens repeatedly but at relatively random intervals. By way of contrast, a pattern corresponding to respiration or a heartbeat, though also typically represented by a short time duration, may be identified at least in part by intervals that are relatively consistent in duration.

Certain patterns may be identified at operation 508 at least in part by their relatively short time durations (e.g., patterns corresponding to certain limb, eye, or heart movements). Certain other patterns may be identified at operation 508 at least in part by their relatively longer durations (e.g., a chest movement corresponding to respiration of a target).

Some patterns may be identified based on their recurring nature. Examples of recurring patterns may be patterns corresponding to heart beats or breathing of a target. Such patterns may be repeated substantially predictably (e.g., with a predictable gap between a first pattern and a second pattern in a series of patterns) or substantially randomly (e.g., a rapid eye movement that is repeated substantially unpredictably), with each repetition having a sufficient similarity to the other repetitions in the series. Whether a repetition is sufficient similar to the other repetition may be determined based on a similarity (e.g., plotted measured data points corresponding to each repetition) transgressing a threshold. The recurring pattern may be identified based on a similarity between a first pattern and a second pattern in a series of patterns, such as a similarity in the length of the first pattern in comparison to the second pattern, a similarity in plotted measurements of between the first pattern and the second pattern, a range of a length of a gap between the first pattern and the second pattern, a similarity in wave forms between the first pattern and the second pattern, and so on. Examples of recurring patterns are shown by the plots of data points in FIG. 9-12.

At operation 510, a determination may be made as to whether at least a subset of the data being analyzed deviates from a recurring pattern by an amount exceeding a particular threshold. As shown by the plot of data points in FIG. 11-12, for example, a determination may be made that a characteristic of certain outlier data points deviate by an amount exceeding a particular threshold from a recurring pattern associated with a heart rate. In certain embodiments, the subset of data analyzed at operation 510 may be compared to historical data used at operation 508 to identify a pattern. Although in this example an analysis is performed with respect to a recurring pattern, in alternative embodiments the analysis may not involve a recurring pattern as a reference. For example, a deviation may be identified based on a property of a subset of data that is unusual in comparison to other portions of the data, such as, for example, a deviation beyond a six-sigma threshold or some other expected range.

Figure 6:
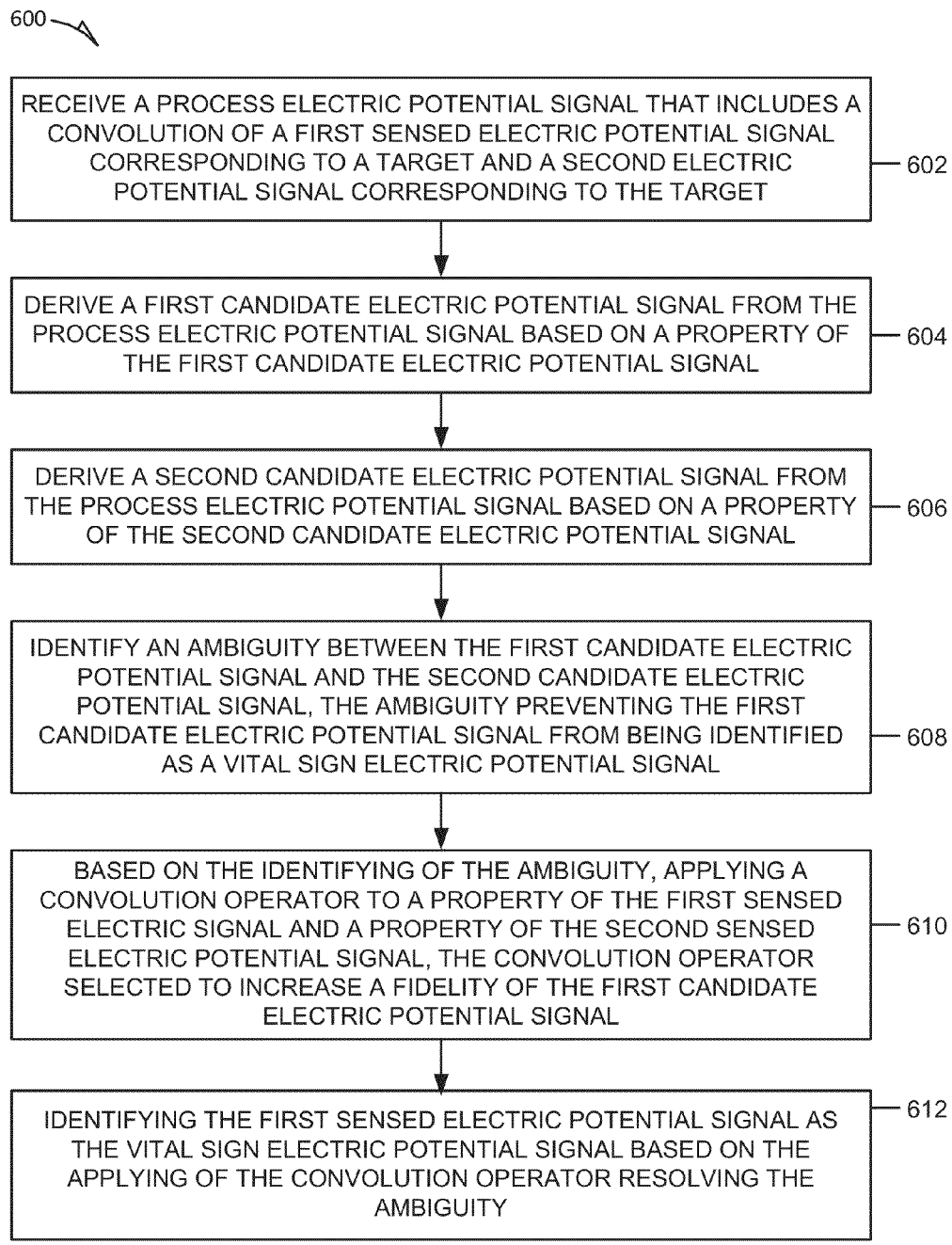
FIG. 6 is a flowchart depicting an example method of increasing fidelity of an electric potential signal.

FIG. 6 is a flowchart depicting an example method 600 of increasing a fidelity of an electric potential signal. In various embodiments, the method 600 may be implemented by one or more of the modules of FIG. 1-4. At operation 602, a signal is received. In certain instances, the received signal may be a conditioned signal 406 in the form of computer-readable data having a particular format suitable for processing by one or more microcontroller unit(s) of module 110. The received signal may include, for example, a convolution of data corresponding to at least (1) a first sensed electric potential signal corresponding to a target, and (2) a second electric potential signal corresponding to the target.

At operation 604, a first candidate electric potential signal is derived from the signal received at operation 602 based on a property of the first candidate electric potential signal. At operation 606, a second candidate electric potential signal is derived from the signal received at operation 602 based on a property of the second electrical potential signal. In various embodiments, the first candidate electric potential signal and the second candidate potential electric signal are derived based on an identification of a disturbance in an electrical field that is distinguished from background disturbances in an environment of the target. In various embodiments, the first candidate electric potential signal and the second candidate electric potential signal are derived based on one or more similarities of the properties of the candidate electric potential signals and the properties of previously-identified electric potential signals known to correspond to vital signs of a target.

At operation 608, a determination is made as to whether an ambiguity between the property of the first candidate electric potential signal and the property of the second candidate potential signal has prevented the first candidate electric potential signal from being identified as a vital sign electric potential signal. For example, an ambiguity may be identified based on the first candidate electric potential signal and the second candidate electric potential signal being distinguished from background disturbances in an environment of the target, but not being sufficiently distinguished from one another such that a correspondence between the first electric potential signal or the second electric potential signal to a particular vital sign (e.g., a heartbeat) of the target may be identified. That is, an ambiguity may exist when the system determines that there are multiple candidate electric potential signals being derived from the process electric potential signal that may correspond to a particular vital sign and the system does not have enough information (e.g., plotted data points) about the properties of the candidate electric potential signals to determine which of the candidate electric potential signals actually corresponds to the particular vital sign.

At operation 610, based on the determination of the ambiguity, a convolution operator is applied to the first sensed electric signal and a property of the second sensed electric potential signal. The convolution operator may be selected based on its likelihood of increasing a fidelity of the first candidate electric potential signal. At operation 612, the first candidate electric potential signal is identified as the vital sign electric potential signal based on the increasing of the fidelity resolving the ambiguity. For example, upon application of the convolution operator, the system may determine that the plotted data points corresponding to the first candidate potential electric potential signal have enough of a resemblance to predetermined patterns corresponding to the vital sign that the second candidate potential electric signal may now be ruled at as corresponding to the vital sign. Whether the first candidate electric potential signal has enough of a resemblance may be determined based on an analysis of similarities between the plotted data points corresponding to the first potential electric potential signal and the predetermined pattern transgressing a threshold. Or, whether the first candidate electric potential signal has enough of a resemblance may be determined based on an analysis of similarities between the plotted data points corresponding to the second potential signal and the predetermined pattern transgressing a threshold.

In other words, the system may resolve the ambiguity by determining that, after the application of the convolution operator, the first candidate electric potential signal is sufficiently similar to a predetermined pattern that the second candidate electric potential signal may be ruled out as corresponding to the vital sign. Or the system may resolve the ambiguity by determining that, after applying the convolution operator, the second candidate electric potential signal is sufficiently dissimilar to the predetermined pattern that the second candidate electric potential signal may be ruled out as corresponding to the vital sign.

In various embodiments, the ambiguity may be resolved by applying a convolution operator to the candidate electric potential signal and an additional candidate electric potential signal, the additional candidate electric potential signal being identified in an additional process electric potential signal derived from an additional electric field disturbance sensor. In other words, a candidate electric potential signal of a first process signal may be disambiguated from additional candidate electric potential signals of the first process signal by enhancing the candidate process electric signal based on electric potential signals in a second electric potential process signal that are identified (e.g., based on wavelet analysis) as corresponding to the candidate electric signal of the first electric potential process signal.

In various embodiments, the determination that a wave or signal in a process signal corresponds to a vital sign of the target includes comparing the waves detected by the sensors at a non-contact distance from the target with well-known waves, such as the P, Q, R, S, T waves of a heart muscle, as they would be detected by a sensor that is placed in contact with the target (e.g., by an ECG). In other words, signals sensed by an electric field disturbance sensor from a non-contact distance may have enough characteristics that are similar to well-known characteristics of different signals sensed by a different type of sensor (e.g., an ECG sensor) that a correspondence between the signals may be identified. That is, upon a threshold in similarity between the characteristics of the different waves of the different signal types being reached, the system 100 may identify a correspondence between the waves and thus identify a particular wave of a process signal as corresponding to a particular well-known vital sign signal.

In various embodiments, the active filtering method discussed above with respect to FIG. 6 may also be used to increase the fidelity of a candidate signal.

In various embodiments, a fidelity of a process signal may be effected by a sensitivity setting controlled by the user of the system 100. The sensitivity setting, for example, may reduce the sensitivity of the electric field disturbance sensor(s) 106 at a particular frequency of mains power (e.g., 50 Hz or 60 Hz). This changing of sensitivity, for example, may enable the user to control whether the system 100 is configured to more accurately monitor the whole body movements of the target or more accurately monitor particular vital signs (e.g., heart or eye movements of the target), such as in an environment in which a tradeoff must be made between the two types of monitoring.

Figure 7:
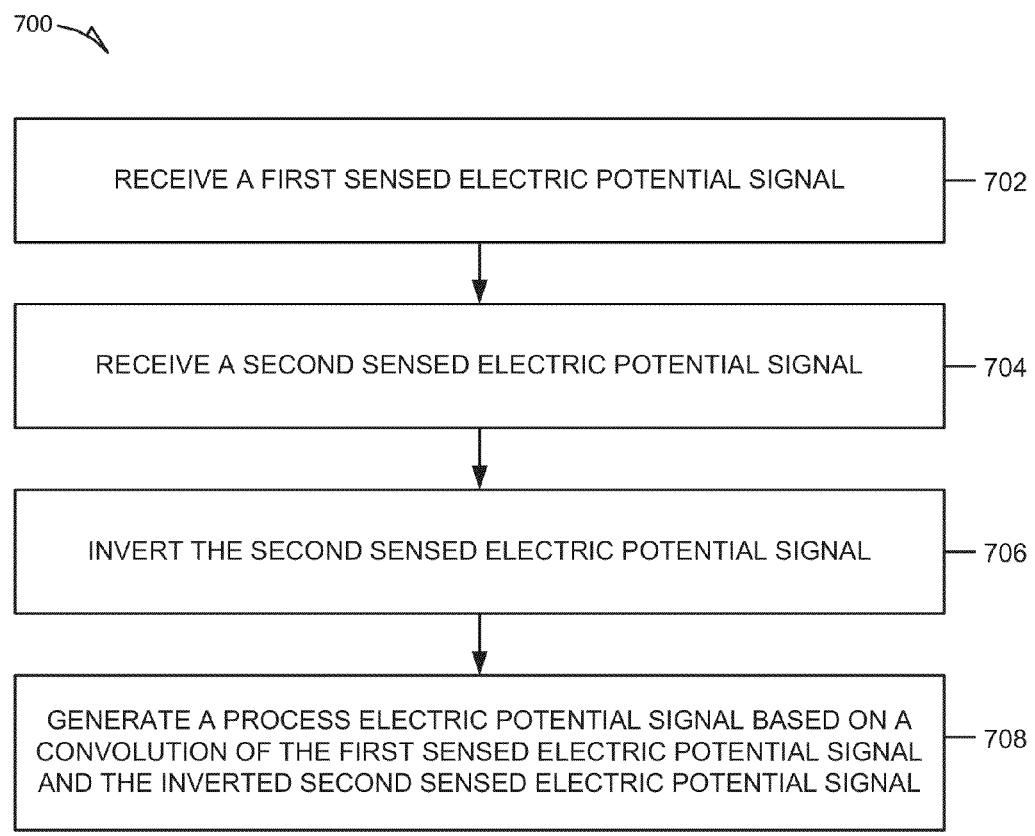
FIG. 7 is a flowchart depicting an example embodiment of a method of generating a process electric potential signal.

FIG. 7 is a flowchart depicting an example method 700 of generating a process electric potential signal. In various embodiments, the method 700 may be implemented by one or more of the modules of FIG. 1-4. At operation 702, a first sensed electric potential signal is received, the first sensed electric potential signal being derived from an electric field associated with a target. At operation 704, a second sensed electric potential signal is received, the second sensed electric potential signal being derived from an ambient electric field in a vicinity of the target. At operation 706, an inverted electric potential signal is generated from the second sensed electric potential signal. At operation 708, the process electric potential signal is generated based on a convolution of the inverted electric potential signal and the first sensed electric potential signal.

Figure 8:
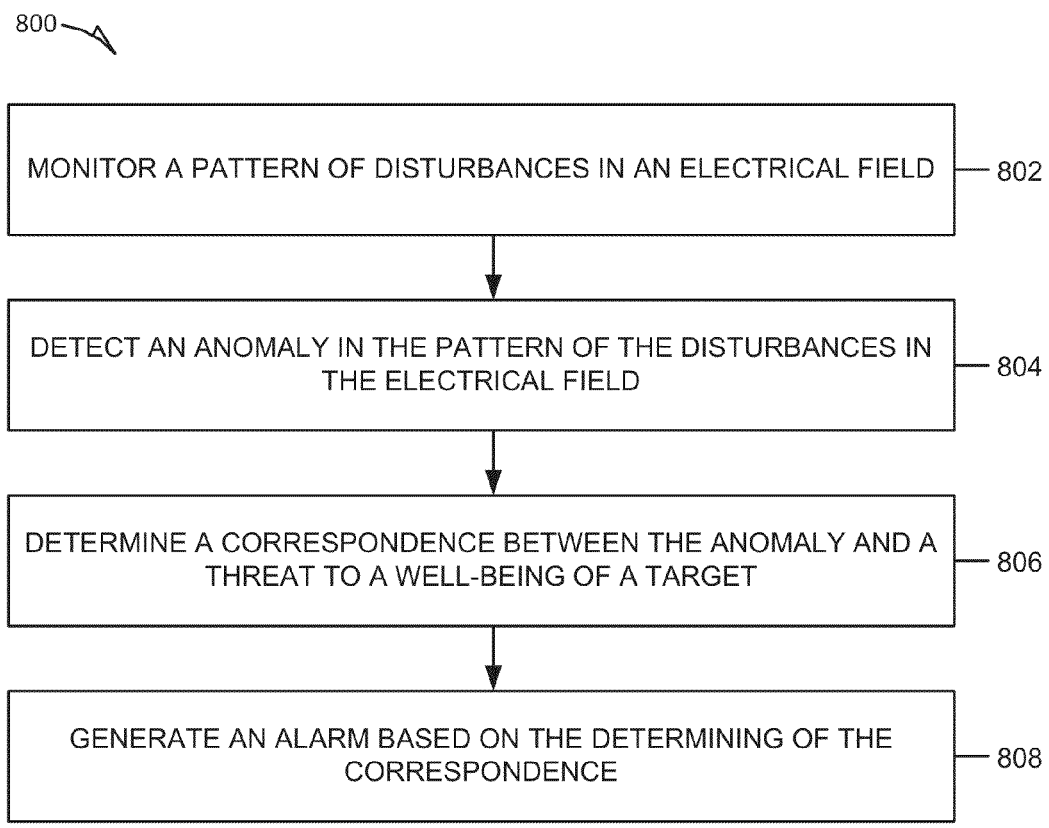
FIG. 8 is a flowchart depicting an example method of generating an alarm based on a detection of an anomaly in a pattern of disturbances in an electrical field.

FIG. 8 is a flowchart depicting an example method of generating an alarm based on a detection of an anomaly in a pattern of disturbances in an electrical field. In various embodiments, the method 800 may be implemented by one or more of the modules of FIG. 1-4. At operation 802, a pattern of disturbances in an electrical field is monitored. For example, the pattern of disturbances may correspond to a candidate electric potential signal that has been identified as a vital sign electric potential signal, as described in FIG. 5-7. In various embodiments, the pattern of disturbances is detected in three dimensions (e.g., based on input from a plurality of sensors).

At operation 804, an anomaly in the pattern of the disturbances in the electrical field is detected. For example, an anomaly is detected in a pattern of disturbances corresponding to brain activity, heart activity, body movements, or eye (or eyelid) movements of the target. For example, the detection of the anomaly may be based on a comparison between the detected pattern and a reference pattern, as described above. In various embodiments, the reference pattern is a three-dimensional pattern.

At operation 806, a correspondence between the anomaly and a threat to the well-being of the target is determined. For example, it is determined that the activity level of the brain of the target (or a region of the brain) has dropped below a predetermined threshold value for a predetermined amount of time. Or it is determined that the heart rate of the individual has dropped below a predetermined threshold value (e.g., 30 beats per minute) for a predetermined amount of time (e.g., two minutes). Or it is determined that the body of the target has moved into a position that the body of the target has not been previously observed in. Or it is determined that the body of the target has not moved for a predetermined amount of time. Or it is determined that the eyelids of the target are moving at a slower-than-average rate for a predetermined amount of time.

At operation 808, an alarm is generated based on the determining of the correspondence between the anomaly and the threat to the well-being of the target. For example, the system emits a loud sound (e.g., like a fire alarm or digital clock alarm) or otherwise performs an action sufficient to notify a caretaker of the target of the detected emergency.

Figure 9:
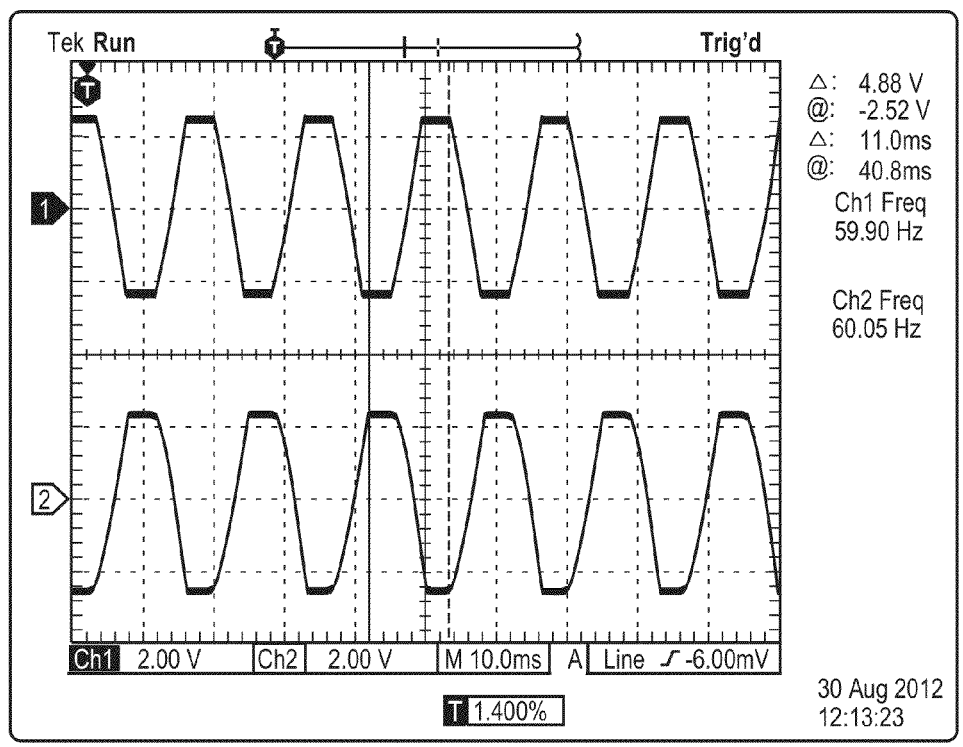
FIG. 9 is a chart depicting a plotting of data corresponding to signals received from one or more sensors of the system of FIG. 1 according to a particular embodiment.

FIG. 9 is a chart depicting a plotting of data corresponding to signals received from one or more sensors 106. In various embodiments, there may be high levels of background 60 Hz noise in an environment of a target. For example, high levels of background noise may be detected in a signal received from a single sensor 106 placed at a distance from a target. In various embodiments, the high levels of background 60 Hz noise may saturate amplifiers at gains that deliver signals corresponding to vital signs of the target. The plot at the top of the chart represents the background noise signal whereas the plot at the bottom of the chart represents a bandpass output signal.

Figure 10:
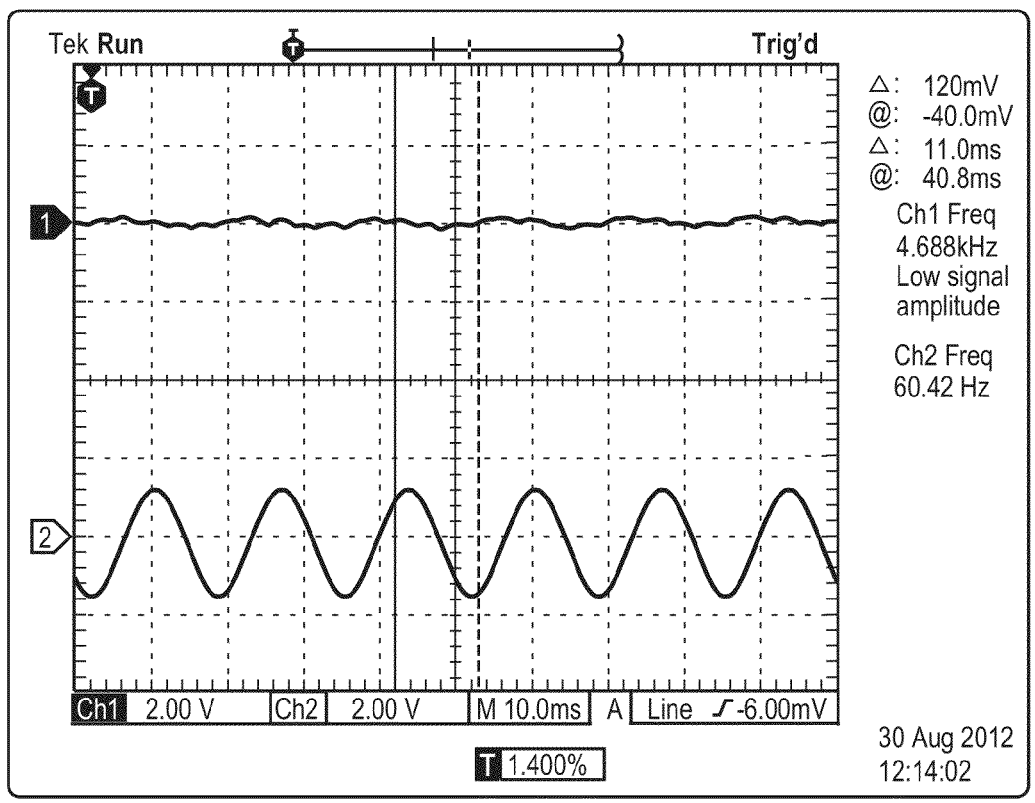
FIG. 10 is a chart depicting a plotting of data corresponding to signals received from one or more sensors of the system of FIG. 1, in which saturating noise has been suppressed according to a particular embodiment.

FIG. 10 is a chart depicting a plotting of data corresponding to signals received from one or more sensors 106 in which saturating noise has been suppressed. In various embodiments, such suppression may be accomplished with the use of a 60 Hz+ harmonics bandpass filter. For example, the 60 Hz+ harmonics bandpass filter may feed its output into the negative input of the sensor. As can be seen from a comparison of plotted data points in FIGS. 9 and 10, suppression of the saturating noise may also reduce the bandpass output.

In various embodiments, switched-capacitor filters may insert a small amount of phase lag in the feedback signal, which may limit the amount of suppression that can be achieved. However, the application of such filters may easily eliminate the amplifier-saturation problem. In various embodiments, an analog low-pass filter on the output may perform additional filtering.

Figure 11:
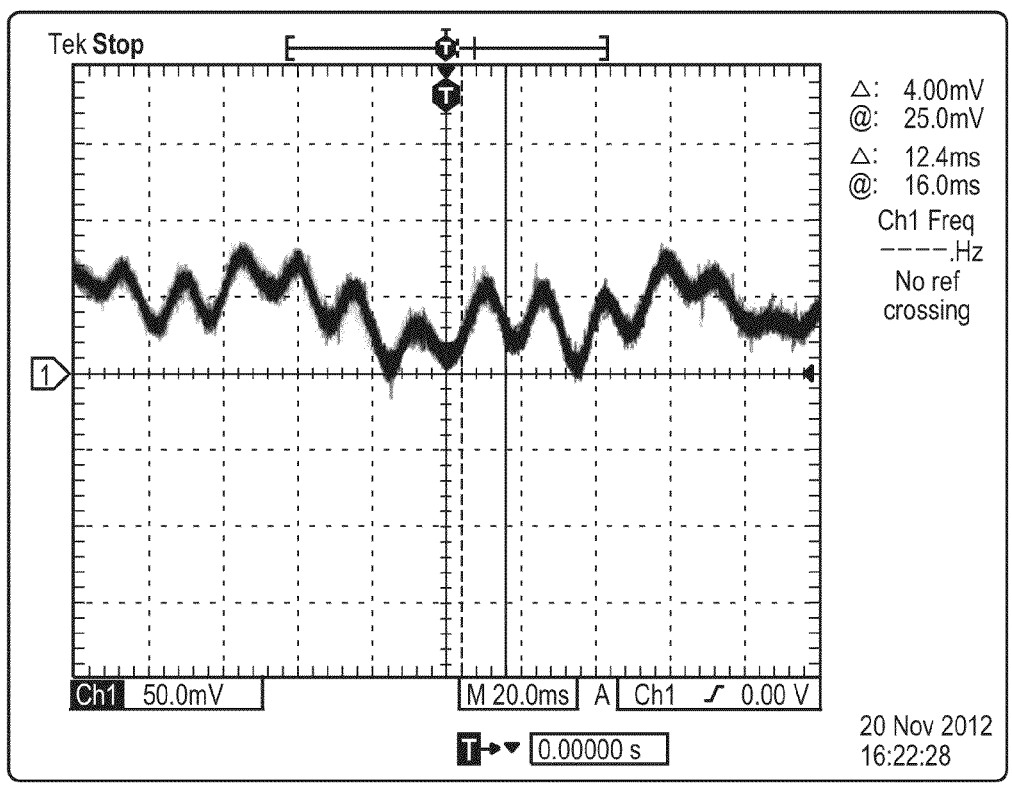
FIG. 11 is a chart depicting a plotting of data corresponding to signals received from one or more sensors of the system of FIG. 1, after the application of certain suppression and low-pass filtering according to a particular embodiment.

FIG. 11 is a chart depicting a plotting of data corresponding to signals received from one or more sensors after the application of suppression and low-pass filtering. In various embodiments, at a proper amplitude scale (e.g., 50 mV/div) and time scale (e.g., 20 ms/div), the residual 60 Hz noise may be viewed after suppression and low-pass filtering.

Figure 12:
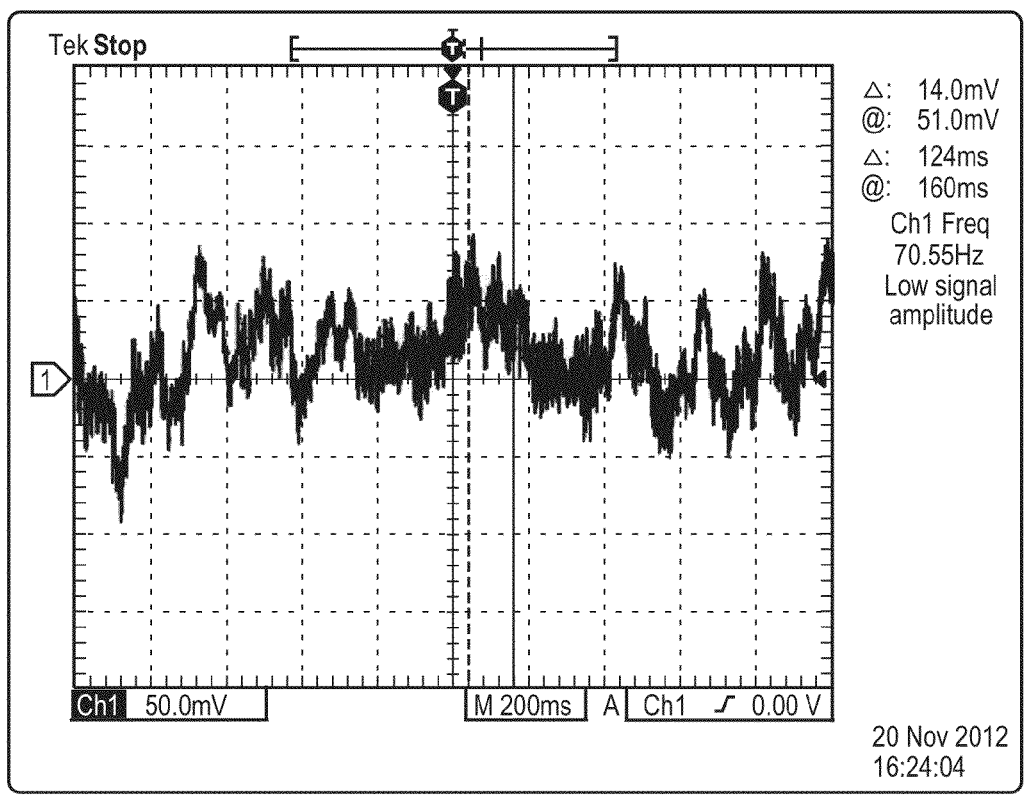
FIG. 12 is a chart depicting a plotting of data corresponding to signals received from one or more sensors after the application of more amplification, suppression, and/or low-pass filtering according to a particular embodiment.

FIG. 12 is a chart depicting a more amplified plotting of data corresponding to signals received from one or more sensors after the application of suppression and low-pass filtering. In various embodiments, signals corresponding to particular vital signs (e.g., EKG signals) may be detected at particular time scales (e.g., 200 ms/div). From a signal received from a sensor placed a few cm from a target, the chart depicts faint suggestions of the EKG complex occurring at 700-800 ms. Further processing, as described above, may discriminate this vital sign signal from background noise in the environment of the target.

Thus, a physio/motion sensor board may suppress the background interference at various frequencies (e.g., 60 Hz), which can saturate a sensitive high-impedance field detection amplifier. Further filtering in a DSP (e.g., a sharp LPF) may remove all noise at the frequency and above. A sharp HPF may remove body-motion artifacts. Then, vital sign signals may be detected at a non-contact range from the target. Use of multiple sensors (e.g., in a differential arrangement) may further improve the signal detection of the system (e.g., by increasing the fidelity of a vital sign signal).

Figure 13:
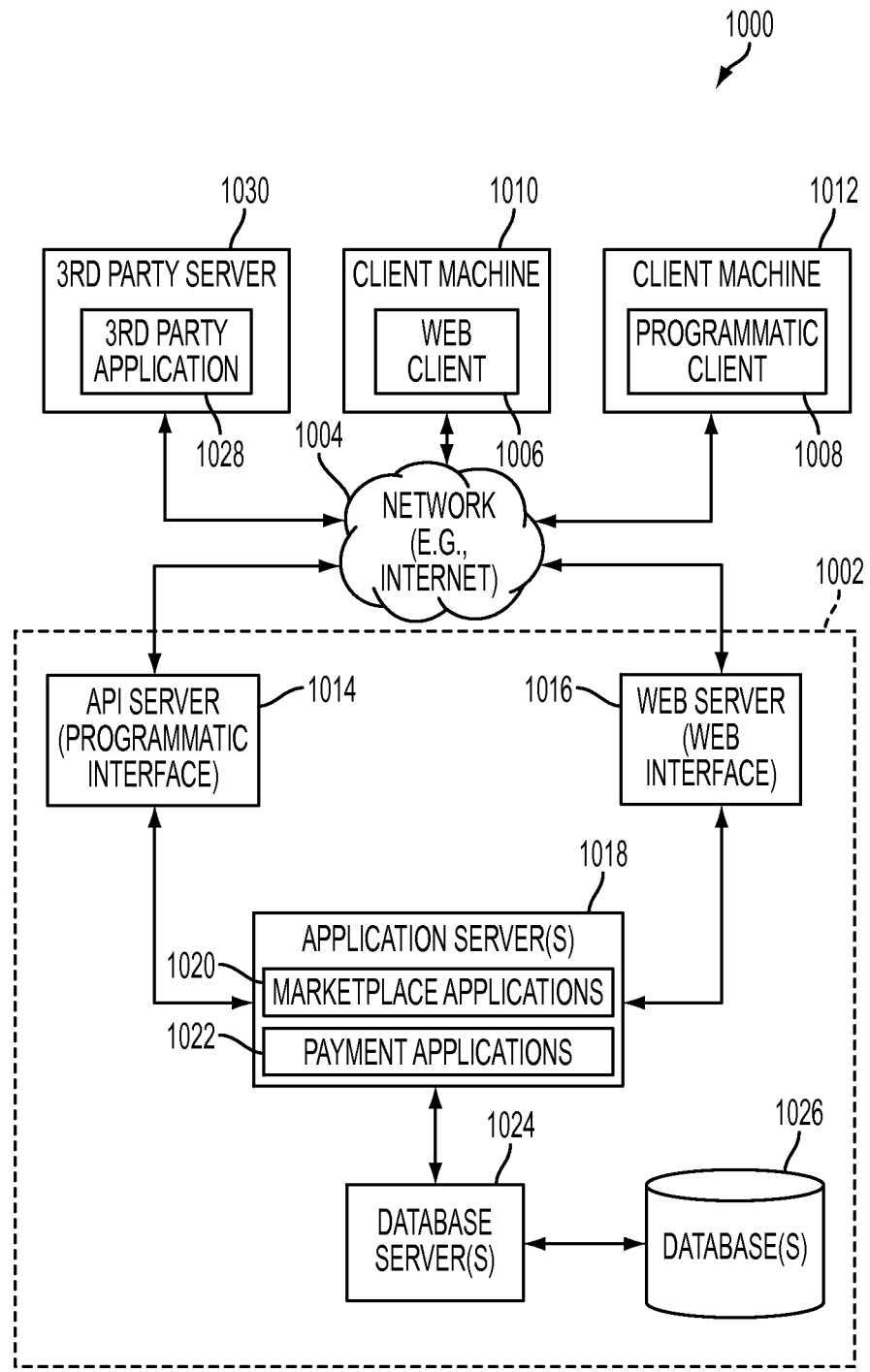
FIG. 13 is a network diagram depicting a client-server system within which various example embodiments may be deployed according to a particular embodiment.

FIG. 13 is a network diagram depicting a client-server system 1000, within which various example embodiments may be deployed. A networked system 1002, in the example form of a monitoring system, provides server-side functionality, via a network 1004 (e.g., the Internet or Wide Area Network (WAN)) to one or more clients. FIG. 13 illustrates, for example, a web client 1006 (e.g., a browser, such as the Internet Explorer browser developed by Microsoft Corporation of Redmond, Wash.) and a programmatic client 1008 executing on respective client machines 1010 and 1012. In various embodiments, the monitoring system 1002 may be embodied by the system 100 of FIG. 1.

Each of the one or more clients may include a software application module (e.g., a plug-in, add-in, or macro) that adds a specific service or feature to a larger system. The software application module may be separate from, though optionally may be integrated in whole or in part with, a user interface and functionality of a software application, such as a spreadsheet application. The software application may be a client software application executing on a client machine. The software application module may be optionally deployed in the same environment as the software application such that the software application module can be accessed from within the software application. The software application module may be optionally enabled or disabled within the environment (e.g., user interface) of the software application. The software application module may appear to be a part of the software application by, for example, providing user interface components or widgets (e.g., menus, toolbars, menu commands, toolbar commands, and so on) that can be enabled, disabled, added to, or removed from standard user interface components or widgets provided by the software application.

An API server 1014 and a web server 1016 are coupled to, and provide programmatic and web interfaces respectively to, one or more application servers 1018. The application servers 1018 host one or more marketplace applications 1020 and payment applications 1022. The application servers 1018 are, in turn, shown to be coupled to one or more database servers 1024 that facilitate access to one or more databases 1026 or NoSQL or non-relational data stores.

The applications 1020 may provide a number of functions and services to users that access the networked system 1002. While the applications 1020 are shown in FIG. 13 to both form part of the networked system 1002, in alternative embodiments, the applications 1020 may form part of a system that is separate and distinct from the networked system 1002. As an example, various modules depicted in FIG. 1 or FIG. 4 may be implemented as or included in applications 1020.

Further, while the system 1000 employs a client-server architecture, various embodiments are, of course, not limited to such an architecture, and could equally well find application in a distributed, or peer-to-peer, architecture system, for example. The various applications 1020 could also be implemented as standalone software programs, which do not necessarily have networking capabilities. Additionally, although FIG. 13 depicts machines 1030, 1010, and 1012 as being coupled to a single networked system 1002, it will be readily apparent to one skilled in the art that machines 1030, 1010, and 1012, as well as application 1028 and clients 1006 and 1008, may be coupled to multiple networked systems.

The web client 1006 accesses the various applications 1020 via the web interface supported by the web server 1016. Similarly, the programmatic client 1008 accesses the various services and functions provided by the applications 1020 via the programmatic interface provided by the API server 1014. The programmatic client 1008 may, for example, be an application executing on an iPhone that enables a user to control the system 100 of FIG. 1 remotely.

FIG. 13 also illustrates a third-party application 1028, executing on a third-party server machine 1030, as having programmatic access to the networked system 1002 via the programmatic interface provided by the API server 1014. For example, the third-party application 1028 may, utilizing information retrieved from the networked system 1002, support one or more features or functions on a website hosted by the third party. The third-party website may, for example, provide one or more functions that are supported by the relevant applications of the networked system 1002.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the network 104) and via one or more appropriate interfaces (e.g., APIs).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 14:
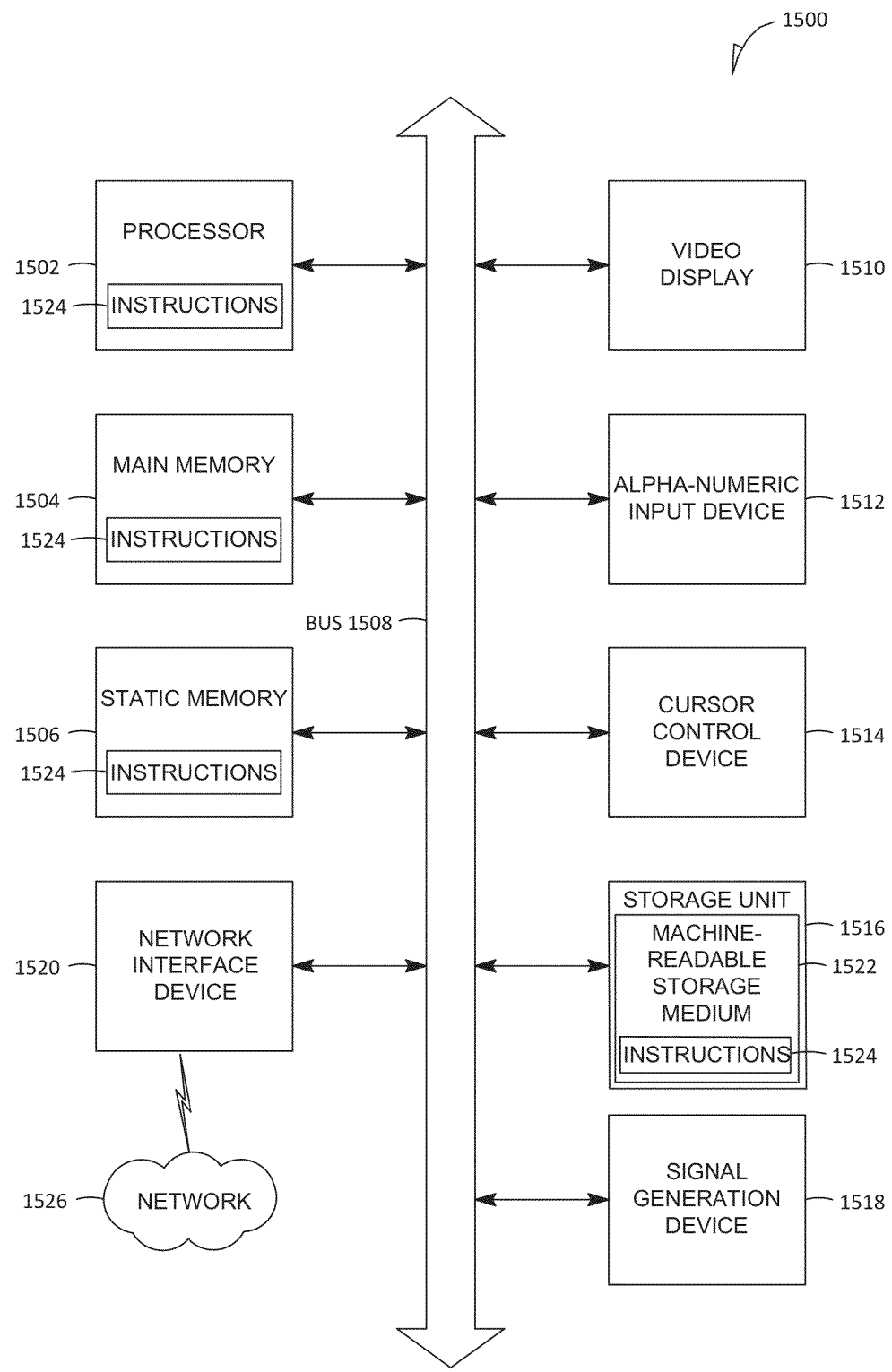
FIG. 14 is a block diagram of machine in the example form of a computer system within which instructions for causing the machine to perform any one or more of the methodologies discussed herein may be executed.

FIG. 14 is a block diagram of machine in the example form of a computer system 1500 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1500 includes a processor 1502 (e.g., a central processing unit (CPU), a graphics processing unit (GPU) or both), a main memory 1504 and a static memory 1506, which communicate with each other via a bus 1508. The computer system 1500 may further include a video display unit 1510 (e.g., a liquid crystal display (LCD) or a cathode ray tube (CRT)). The computer system 1500 also includes an alphanumeric input device 1512 (e.g., a keyboard), a user interface (UI) navigation (or cursor control) device 1514 (e.g., a mouse), a storage (e.g., disk drive) unit 1516, a signal generation device 1518 (e.g., a speaker) and a network interface device 1520.

The disk drive unit 1516 includes a machine-readable medium 1522 on which is stored one or more sets of data structures and instructions (e.g., software) embodying or utilized by any one or more of the methodologies or functions described herein. The instructions 1524 may also reside, completely or at least partially, within the main memory 1504 and/or within the processor 1502 during execution thereof by the computer system 1500, the main memory 1504 and the processor 1502 also constituting machine-readable media. The instructions 1524 may also reside, completely or at least partially, within the static memory 1506.

While the machine-readable medium 1522 is shown in an example embodiment to be a single medium, the term "machine-readable medium" may include a single medium or multiple media (e.g., a centralized or distributed database, and/or associated caches and servers) that store the one or more instructions 1524 or data structures. The term "machine-readable medium" shall also be taken to include any tangible medium that is capable of storing, encoding or carrying instructions for execution by the machine and that cause the machine to perform any one or more of the methodologies of the present embodiments, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and compact disc-read-only memory (CD-ROM) and digital versatile disc (or digital video disc) read-only memory (DVD-ROM) disks.

The instructions 1524 may further be transmitted or received over a communications network 1526 using a transmission medium. The instructions 1524 may be transmitted using the network interface device 1520 and any one of a number of well-known transfer protocols (e.g., HTTP). Examples of communication networks include a LAN, a WAN, the Internet, mobile telephone networks, POTS networks, and wireless data networks (e.g., WiFi and WiMax networks). The term "transmission medium" shall be taken to include any intangible medium capable of storing, encoding or carrying instructions for execution by the machine, and includes digital or analog communications signals or other intangible media to facilitate communication of such software. In various embodiments, the network 1526 may correspond to the network 1004.

Certain embodiments disclosed herein may be integrated in whole or in part with each other. For example, the system 100 of FIG. 1 may be an example embodiment of, or form at least a portion of, the computer system 1500 of FIG. 14, and vice versa.

Although an embodiment has been described with reference to specific example embodiments, it will be evident that various modifications and changes may be made to these embodiments without departing from the broader spirit and scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
electronically receiving, by a computer system, data representing a signal generated at least in part by one or more sensors detecting a change in an electric field or an electric potential of a target spaced apart from the one or more sensors;
identifying, using the computer system and based at least in part on the data electronically received by the computer system, a recurring pattern in the data; and
determining, using the computer system and based at least in part on the data electronically received by the computer system, whether a deviation from the recurring pattern transgresses a threshold, the deviation comprising a subset of the data electronically received by the computer system.

2. The method of claim 1, wherein the change in the electric field or the electric potential is caused by at least one of a physiological movement and a non-physiological movement of the target.

3. The method of claim 1, wherein the one or more sensors detecting the change in the electric field or the electric potential of a target spaced apart from the one or more sensors, detect a change in capacitance of the target.

4. The method of claim 1, further comprising determining the threshold based at least in part on the recurring pattern, such that the threshold corresponds to a threat to the well-being of the target.

5. The method of claim 1, wherein the recurring pattern is based at least in part on an estimated position of the target in three-dimensional space.

6. The method of claim 1, further comprising generating an alarm based at least in part on a determination that the deviation from the recurring pattern transgresses the threshold, the alarm indicating a threat to the well-being of the target.

7. The method of claim 1, wherein the recurring pattern corresponds to a vital sign of the target.

8. The method of claim 1, wherein the recurring pattern corresponds to a movement of the target and wherein the deviation is caused at least in part by a particular movement of the target.

9. The method of claim 1, wherein the recurring pattern corresponds to a recurring muscular movement of the target.

10. The method of claim 9, wherein the recurring muscular movement comprises eye movement.

11. The method of claim 1, wherein the signal includes a convolution of a plurality of signals received from a plurality of the one or more sensors, the convolution of the plurality of signals describing the recurring pattern of the disturbances in the electric field or the electric potential in a three-dimensional space.

12. The method of claim 11, further comprising filtering the signal based at least in part on an application of a convolution operator applied to the convolution of the plurality of signals.

13. A system comprising:
a memory; and
one or more processors coupled to the memory, the one or more processors configured to, based on instructions contained in the memory:
electronically receive data representing a signal generated at least in part by one or more sensors detecting a change in an electric field or an electric potential of a target spaced apart from the one or more sensors,
identify, based at least in part on the data electronically received, a recurring pattern in the data representing a signal, and
determine, based at least in part on the data electronically received, whether a deviation from the recurring pattern transgresses a threshold, the deviation comprising a subset of the data electronically received.

14. The system of claim 13, wherein the one or more processors are configured to, based on instructions contained in the memory, determine the change in the electric field or the electric potential caused by at least one of a physiological movement and a non-physiological movement of the target.

15. The system of claim 13, wherein the one or more sensors detecting the change in the electric field or the electric potential of the target spaced apart from the one or more sensors, detect a change in capacitance of the target.

16. The system of claim 13, wherein the one or more processors are configured to, based on instructions contained in the memory, determine the threshold based at least in part on the recurring pattern, such that the threshold corresponds to a threat to the well-being of the target.

17. The system of claim 13, wherein the recurring pattern is based at least in part on an estimated position of the target in three-dimensional space.

18. The system of claim 13, wherein the one or more processors further configured to, based on instructions contained in the memory, generate an alarm based at least in part on a determination that the deviation from the recurring pattern transgresses the threshold, the alarm indicating a threat to the well-being of the target.

19. The system of claim 13, wherein the recurring pattern corresponds to a vital sign of the target.

20. The system of claim 13, wherein the recurring pattern corresponds to a movement of the target and wherein the deviation is caused at least in part by a particular movement of the target.

21. The system of claim 13, wherein the recurring pattern corresponds to a recurring muscular movement of the target.

22. The system of claim 21, wherein the recurring muscular movement comprises eye movement.

23. The system of claim 13, wherein the signal includes a convolution of a plurality of signals received from a plurality of sensors, the convolution of the plurality of signals describing the recurring pattern of the disturbances in the electrical field or the electric potential in a three-dimensional space.

24. The system of claim 23, the one or more processors further configured to, based on instructions contained in the memory, filter the signal based at least in part on an application of a convolution operator applied to the convolution of the plurality of signals.

25. A non-transitory machine-readable medium storing a set of instructions that, when executed by at least one processor, causes the at least one processor to perform operations comprising:
electronically receiving data representing a signal generated at least in part by one or more sensors detecting a change in an electric field or electric potential of a target spaced apart from the one or more sensors;
identifying, based at least in part on the data electronically received, a recurring pattern in the data representing a signal; and
determining, based at least in part on the data electronically received, whether a deviation from the recurring pattern transgresses a threshold, the deviation comprising a subset of the data electronically received.

26. The non-transitory machine-readable medium of claim 25, wherein the change in the electric field or the electric potential is caused by at least one of a physiological movement and a non-physiological movement of the target.

27. The non-transitory machine-readable medium of claim 25, the operations further comprising the one or more sensors detecting the change in the electric field or the electric potential of the target spaced apart from the one or more sensors, detecting a change in capacitance of the target.

28. The non-transitory machine-readable medium of claim 25, the operations further comprising determining the threshold based at least in part on the recurring pattern, such that the threshold corresponds to a threat to the well-being of the target.

29. The non-transitory machine-readable medium of claim 25, wherein the recurring pattern is based at least in part on an estimated position of the target in three-dimensional space.

30. The non-transitory machine-readable medium of claim 25, the operations further comprising generating an alarm based at least in part on a determination that the deviation from the recurring pattern transgresses the threshold, the alarm indicating a threat to the well-being of the target.

31. The non-transitory machine-readable medium of claim 25, wherein the recurring pattern corresponds to a vital sign of the target.

32. The non-transitory machine-readable medium of claim 25, wherein the recurring pattern corresponds to a movement of the target and wherein the deviation is caused at least in part by a particular movement of the target.

33. The non-transitory machine-readable medium of claim 25, wherein the recurring pattern corresponds to a recurring muscular movement of the target.

34. The non-transitory machine-readable medium of claim 33, wherein the recurring muscular movement comprises eye movement.

35. The non-transitory machine-readable medium of claim 25, wherein the signal includes a convolution of a plurality of signals received from a plurality of the one or more sensors, the convolution of the plurality of signals describing the recurring pattern of the disturbances in the electrical field or the electric potential in a three-dimensional space.

36. The non-transitory machine-readable medium of claim 25, the operations further comprising filtering the signal based at least in part on an application of a convolution operator applied to the convolution of the plurality of signals.

* * * * *